United States Patent [19]

Sanderson

[11] Patent Number: 4,818,541

[45] Date of Patent: Apr. 4, 1989

[54] TRANSDERMAL DELIVERY OF ENANTIOMERS OF PHENYLPROPANOLAMINE

[75] Inventor: John E. Sanderson, North Miami, Fla.

[73] Assignee: Schering Corporation, Kenilworth, N.J.

[21] Appl. No.: 87,848

[22] Filed: Aug. 19, 1987

[51] Int. Cl.$^4$ ............................................. A61F 13/02
[52] U.S. Cl. ..................................... 424/448; 424/449
[58] Field of Search .............................. 424/449, 448

[56] References Cited

U.S. PATENT DOCUMENTS

| | | | |
|---|---|---|---|
| 4,292,301 | 9/1981 | Keith et al. | 424/486 |
| 4,294,820 | 10/1981 | Keith et al. | 424/449 |
| 4,532,244 | 7/1985 | Innes | 514/291 |

FOREIGN PATENT DOCUMENTS 8600814  2/1986  PCT Int'l Appl. .

OTHER PUBLICATIONS

J. C. Blosser et al, *Eur. J. Pharmacology*, 134 (1987), pp. 97–103.
A. S. Michaels et al, *AIChE J.*, 21 (1975), pp. 985–996.

*Primary Examiner*—Thurman K. Page
*Assistant Examiner*—L. R. Horne
*Attorney, Agent, or Firm*—Anita W. Magatti; James R. Nelson; Stephen I. Miller

[57] ABSTRACT

A method of inducing anorexia or nasal decongestion comprising transdermally administering an enantiomer of phenylpropanolamine is disclosed.

16 Claims, No Drawings

TRANSDERMAL DELIVERY OF ENANTIOMERS OF PHENYLPROPANOLAMINE

The present invention relates to transdermal delivery of the optical isomers of phenylpropanolamine.

More particularly, the invention relates to the transdermal delivery of an optical isomer of phenylpropanolamine for use as an anorectic or nasal decongestant.

BACKGROUND OF THE INVENTION

Phenylpropanolamine is a sympathomimetic compound administered orally as an anorectic and as a nasal decongestant. The compound has two chiral centers, as shown in the following structural formula:

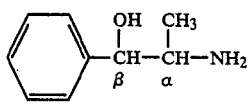

This results in four optical isomers, listed as follows with their common names and absolute configurations:

| Isomer | α | β |
|---|---|---|
| (+)-norephedrine | R | S |
| (−)-norephedrine | S | R |
| (+)-norpseudoephedrine | S | S (Cathine) |
| (−)-norpseudoephedrine | R | R |

The β center is optically stronger and is responsible for the observed rotation. The α center, however, is primarily responsible for determining the physiological effect of the compound. An R configuration at this position gives a compound with predominantly peripheral effects (vasoconstriction, etc.), whereas compounds with an S configuration have greater central nervous system (CNS) activity. Since the anorectic effect is CNS-mediated, one would expect (−)-norephedrine and (+)-norpseudoephedrine to be the most potent in this regard. (+)-Norpseudoephedrine is a naturally occurring substance found primarily in the shrub *Catha edulis* and is used orally in Europe for its anorectic properties at a dose of about 40-50 mg/day. A racemic mixture of (+)-norephedrine and (−)-norephedrine, generally referred to as phenylpropanolamine (PPA), is marketed domestically as an anorectic at a dose of about 50-75 mg/day, and as a nasal decongestant at a dose of about 75-225 mg/day, preferably about 150-200 mg/day for adults.

Transdermal delivery of drugs has become increasingly well known as the technology to manufacture transdermal delivery systems advances. Transdermal devices such as reservoir, matrix and adhesive patches are well known. The advantages of transdermal delivery are also well known and include the practical advantages of ease of use and greater patient compliance and the pharmacological advantage of sustained blood levels. It has been reported by A. S. Michaels et al in *AIChE J.*, 21 (1975), pgs. 985-996, that ephedrine, an N-methyl derivative of PPA, penetrates cadaver skin at a rate of 300 mg/cm²/hr. While the article does not state whether "ephedrine" refers to the racemate or an isomer, it is believed to refer to (−)-ephedrine, since that isomer is the conventional commercially available form. A more recent article, J. C. Blosser et al, *Eur. J. Pharmacology*, 134 (1987) pgs. 97-103 indicates that when administered orally, the enantiomers of PPA showed a 4-5 fold difference in potency, the order being (+)-norpseudoephedrine, (−)-norephedrine, (−)-norpseudoephedrine and (+)-norephedrine (highest to lowest).

DETAILED DESCRIPTION

The present invention relates to the surprising superiority of the transdermal penetration of the individual optical isomers of PPA compared to racemic PPA ((±)-norephedrine).

(±)-Phenylpropanolamine (a mixture of (+)- and (−)-norephedrine) was found to have a transdermal flux of 16 μg/cm²/hour measured by cadaver skin flux from a saturated aqueous donor solution at 32° C. (solubility 44.5 mg (±)-PPA/ml). In comparison, 50% w/w aqueous donor solutions of the individual enantiomers exhibit about ten times that flux:

| | |
|---|---|
| (+)-norephedrine | 150 ug/cm²/hr |
| (−)-norephedrine | 160 ug/cm²/hr |
| (+)-norpseudoephedrine | 160 ug/cm²/hr |
| (−)-norpseudoephedrine | 160 ug/cm²/hr |

Passive transdermal flux was measured using heat separated cadaver epidermis in quadruplicate in Franz cells. In each case the receiver solution was 0.15M saline buffered to pH 7.4 with 0.01M phosphate.

The PPA and its enantiomers were converted to the free base form from the corresponding hydrochlorides when necessary by neutralization and precipitation from aqueous solution.

One can see from the above results that the transdermal fluxes of the four isomers are essentially equivalent for a given donor solution concentration. All of the isomers are extremely water soluble, but the recrystallization behavior of these isomers suggests that the norephedrine isomers are more soluble. Thus a higher donor solution concentration of these isomers is possible, which may result in a higher achievable transdermal flux for the norephedrines. Nevertheless, the fluxes obtained at the donor solution concentration tested indicate that any of these isomers could be delivered transdermally from a patch with ten to twenty square centimeters of active area to provide an anorectic dosing rate comparable to the oral dosing rate commonly used with the racemic compound (i.e., about 50-75 mg/day), which rate could only be achieved by an impractically large (i.e., greater than 100 cm²) patch using the less soluble racemate.

Although these compounds are suspected of having some direct physiological activity, both their anorectic and nasal decongestant effects are apparently mediated by norepinephrine release. Since (−)-norephedrine has the same stereochemical configuration as naturally occurring norepinephrine, one would expect this to be the more potent isomer. However, norepinephrine release mechanism is also responsible for the primary drawback of the oral anorectic PPA preparations currently on the market. That is, once the PPA blood levels drop, the patient is left in a state of depleted free norepinephrine levels, resulting in an increase in appetite. Midnight raids on the refrigerator are a fairly common occurrence with this therapy, since the oral preparations only last for up to sixteen hours. Transdermal administration, however, could easily maintain the necessary blood levels for a full twenty-four hours or more.

(+)-Norpseudoephedrine has already been approved as an anorectic for oral use abroad, but has reportedly been withdrawn from the over-the-counter market because of abuse. Transdermal delivery would significantly reduce such an abuse potential by eliminating the peak blood levels associated with oral use.

The use of a particular transdermal formulation is not critical to the practice of this invention in its broadest aspects. Thus, the invention contemplates the use of any formulation, including those not yet discovered or fully characterized, so long as the transdermal dosage form can be used to transdermally deliver the required amount of the desired isomer of PPA.

A preferred transdermal delivery formulation is an adhesive bilayer transdermal dosage layer such as that described in WO86/00814, published Feb. 13, 1986, where the drug is preferably dispersed in a layer of partially cross-linked acrylic adhesive, which layer is adhered to a backing layer, and which is preferably protected until use by a release liner. Other adhesive systems are also well known.

Other suitable transdermal delivery systems include such well known techniques as reservoir and matrix systems, wherein drug flow may be membrane-controlled or diffusion-controlled. An example of a matrix system is disclosed in U.S. Pat. No. 4,294,820 to Keith et al, wherein a polymeric diffusion matrix comprised of a polar plasticizer (e.g. glycerol), a polyvinylalcohol and polyvinylpyrrolidone is used to provide sustained release of phenylephrine.

Following are examples of the preparation of transdermal patches for the administration of an enantiomer of PPA, especially for use as an anorectic. The term "Drug" includes any of the four individual enantiomers.

Example 1

| Adhesive Bilayer Patch Ingredients | Concentrations (% w/w) |
|---|---|
| Acrylic Pressure-Sensitive Adhesive (Monsanto RA-3011)[1] | 30.2 |
| Acrylic Pressure-Sensitive Adhesive (Monsanto RA-2397)[2] | 30.2 |
| Drug | 33.4 |
| Thickener (Union 78 Amsco-Res 6038)[3] | 1.2 |
| Cross-linking Agent (American Cyanamid Aerotex) Resin 3730)[4] | .4 |
| Water | 4.0 |
| | 100.00% |
| Backing layer (SARANEX) | |
| Release liner (Silicone coated polyvinylchloride) | |

[1]Butyl acrylate copolymer (MW 2,000–1,000,000, peak at 65,000) with 0.5% alkyl substituted melamine with emulsifier (36% water.)
[2]Butyl acrylate copolymer (MW 2,000–1,000,000, peak at 47,000) with emulsifier (34% water.)
[3]13% copolymer - sodium polyacrylate.
[4]81% trialkyl melamine derivative, 10% water, 9% MeOH.

Method of Manufacture

1. Combine and mix acrylic adhesives in an appropriate vessel.

2. Add water and mix to form a homogeneous mixture.

3. Add thickener and agitate to form a homogeneous mixture.

4. Add the drug and mix to form a homogeneous mixture.

5. Add the cross-linking agent and agitate thoroughly to effect cross-linking of polymer chains.

6. Transfer the mixture from Step 5 to a coating station, wherein the adhesive-drug mixture is coated (3.5 to 4 mm thick) on the backing layer and the bilayer system is passed into a heating means in order to remove water and/or solvents.

7. Laminate the bilayer system with the release liner.

8. Cut or punch the bilayer system into desired size and shape for unit dosage form.

Example 2

| Matrix Patch Ingredients | Amount |
|---|---|
| Glycerol | 30 gm |
| Polyvinylalcohol (PVA 100% hydrolyzed, MW 115,000) | 15 gm |
| Polyvinylpyrrolidone (MW 40,000) | 8 gm |
| Drug | 2 gm |
| Water | 45 ml |
| Backing layer (polyethylene) | |

Method of Manufacture

1. Mix the glycerol and water and heat to 90° C.; after reaching at least 70° C., add polyvinylalcohol and polyvinylpyrrolidone and stir at 90° C. until solution is effected.

2. Mix 98 ml of solution with 2 gm drug and stir until homogeneous.

3. Pour the mixture into forms made of glass or stainless steel which serve as templates to produce a diffusion matrix having a thickness of 2–3 mm.

4. Apply the matrix to the backing layer.

5. Cut the matrix into the desired size and shape for unit dosage forms.

We claim:

1. A method of inducing anorexia comprising transdermally administering to a human in need of such treatment about 40–50 mg. daily of an anorectic compound selected from the group consisting of (+)-norephedrine, (−)-norephedrine, (+)-norpseudoephedrine and (−)-norpseudoephedrine.

2. A method of claim 1 wherein the anorectic compound is (+)-norephedrine.

3. A method of claim 1 wherein the anorectic compound is (−)-norephedrine.

4. A method of claim 1 wherein the anorectic compound is (+)-norpseudoephedrine.

5. A method of claim 1 wherein the anorectic compound is (−)-norpseudoephedrine.

6. A method of inducing nasal decongestion comprising transdermally administering to a human in need of such treatment about 75 to 225 mg. per day amount of a decongestant compound selected from the group consisting of (+)-norephedrine, (−)-norephedrine, (+)-norspseudoephedrine and (−)-norpseudoephedrine.

7. A method of claim 1 wherein the decongestant compound is (+)-norephedrine.

8. A method of claim 1 wherein the decongestant compound is (−)-norephedrine.

9. A method of claim 1 wherein the decongestant compound is (+)-norpseudoephedrine.

10. A method of claim 1 wherein the decongestant compound is (−)-norpseudoephedrine.

11. A composition of claim 6 wherein the transdermal delivery system is an adhesive layer system.

12. A composition of claim 6 wherein the transdermal delivery system is a matrix system.

13. The method of claim 1 wherein the anorexic compound is administered with a transdermal device.

14. The method of claim 13 wherein the transdermal device is a reservoir, a matrix or an adhesive patch.

15. The method of claim 14 wherein the transdermal device has an active area of about 10 to about 20 square centimeters.

16. The method of claim 14 wherein the anorexic compound is dispersed in an adhesive patch having a layer of partially cross-linked acrylic adhesive.

* * * * *